United States Patent
Welt et al.

(10) Patent No.: US 8,893,733 B2
(45) Date of Patent: Nov. 25, 2014

(54) ERGONOMIC DENTAL FLOSSING DEVICE

(75) Inventors: Theodore Welt, Moshav Shoresh (IL); Jonathan Weisberg, Jerusalem (IL)

(73) Assignee: VeriFresh Ltd., Jerusalem (IL)

( * ) Notice: Subject to any disclaimer, the term of this patent is extended or adjusted under 35 U.S.C. 154(b) by 477 days.

(21) Appl. No.: 11/719,946

(22) PCT Filed: Nov. 23, 2005

(86) PCT No.: PCT/IL2005/001241
§ 371 (c)(1),
(2), (4) Date: Jun. 20, 2007

(87) PCT Pub. No.: WO2006/056978
PCT Pub. Date: Jun. 1, 2006

(65) Prior Publication Data
US 2009/0165814 A1    Jul. 2, 2009

Related U.S. Application Data

(60) Provisional application No. 60/630,462, filed on Nov. 24, 2004, provisional application No. 60/670,275, filed on Apr. 12, 2005.

(51) Int. Cl.
*A61C 15/04*    (2006.01)
*A46B 5/00*    (2006.01)

(52) U.S. Cl.
CPC ............. *A61C 15/046* (2013.01); *A46B 5/0075* (2013.01); *A46B 5/0083* (2013.01); *A46B 2200/1066* (2013.01); *A46B 2200/108* (2013.01); *A61C 15/047* (2013.01)
USPC ......................................................... 132/323

(58) Field of Classification Search
USPC .................................................. 132/323–329
See application file for complete search history.

(56) References Cited

U.S. PATENT DOCUMENTS

| 664,126 A | | 12/1900 | Cowan | |
|---|---|---|---|---|
| 2,187,899 A | * | 1/1940 | Henne | 132/323 |
| 3,892,249 A | * | 7/1975 | Jones et al. | 132/323 |

(Continued)

FOREIGN PATENT DOCUMENTS

| JP | 07-022714 UM | 4/1995 |
|---|---|---|
| JP | 2001 005821 | 4/2001 |

OTHER PUBLICATIONS

Translation of Office Action dated Feb. 1, 2011 by the Japanese Patent Office in corresponding Application No. 2007-542510.

(Continued)

*Primary Examiner* — Robyn Doan

(57) ABSTRACT

A dental flossing device comprising a handle and a floss holder. The floss holder comprises a base portion and a pair of spaced-apart arms accommodating dental floss therebetween. The floss holder has greater flexibility in a direction laterally perpendicular to the direction of the length of said length of dental floss than in the direction of the floss itself. This flexibility is provided either by incorporating at least one convoluted section into either the base portion or the pair of spaced-apart arms of the floss holder, or by providing either the base portion or the pair of spaced-apart arms with a reduced cross sectional dimension in the lateral direction generally perpendicular to the floss than in the direction generally parallel to the floss, or by means of a groove in the neck by which the floss holder is attached to the handle.

18 Claims, 6 Drawing Sheets

(56) References Cited

U.S. PATENT DOCUMENTS

| | | |
|---|---|---|
| 3,927,686 A | 12/1975 | Zambito |
| 4,615,349 A * | 10/1986 | Kukuruzinski ............... 132/323 |
| 5,056,540 A | 10/1991 | Page |
| 5,261,430 A | 11/1993 | Mochel |
| 5,438,726 A * | 8/1995 | Leite ............................. 15/105 |
| 5,483,982 A | 1/1996 | Bennett et al. |
| 5,666,983 A | 9/1997 | McCullough et al. |
| 6,006,762 A | 12/1999 | Hsia |
| 6,138,689 A | 10/2000 | Stern |
| 7,104,266 B2 * | 9/2006 | Lee ............................... 132/323 |
| 7,270,129 B1 * | 9/2007 | Rehkemper .................... 132/322 |
| 7,478,958 B2 * | 1/2009 | Ramet ........................... 401/124 |
| 2003/0056311 A1 | 3/2003 | Broecker et al. |
| 2004/0094182 A1 * | 5/2004 | Forsell .......................... 132/327 |
| 2005/0284501 A1 * | 12/2005 | Rehkemper .................... 132/322 |

OTHER PUBLICATIONS

Translaion of Office Action dated Aug. 16, 2011 by the Japanese Patent Office in corresponding Application No. 2007-542510.
Extended Supplementary Search Report issued on Sep. 12, 2012 by the EPO, in corresponding EP application No. 05809251.1.

* cited by examiner

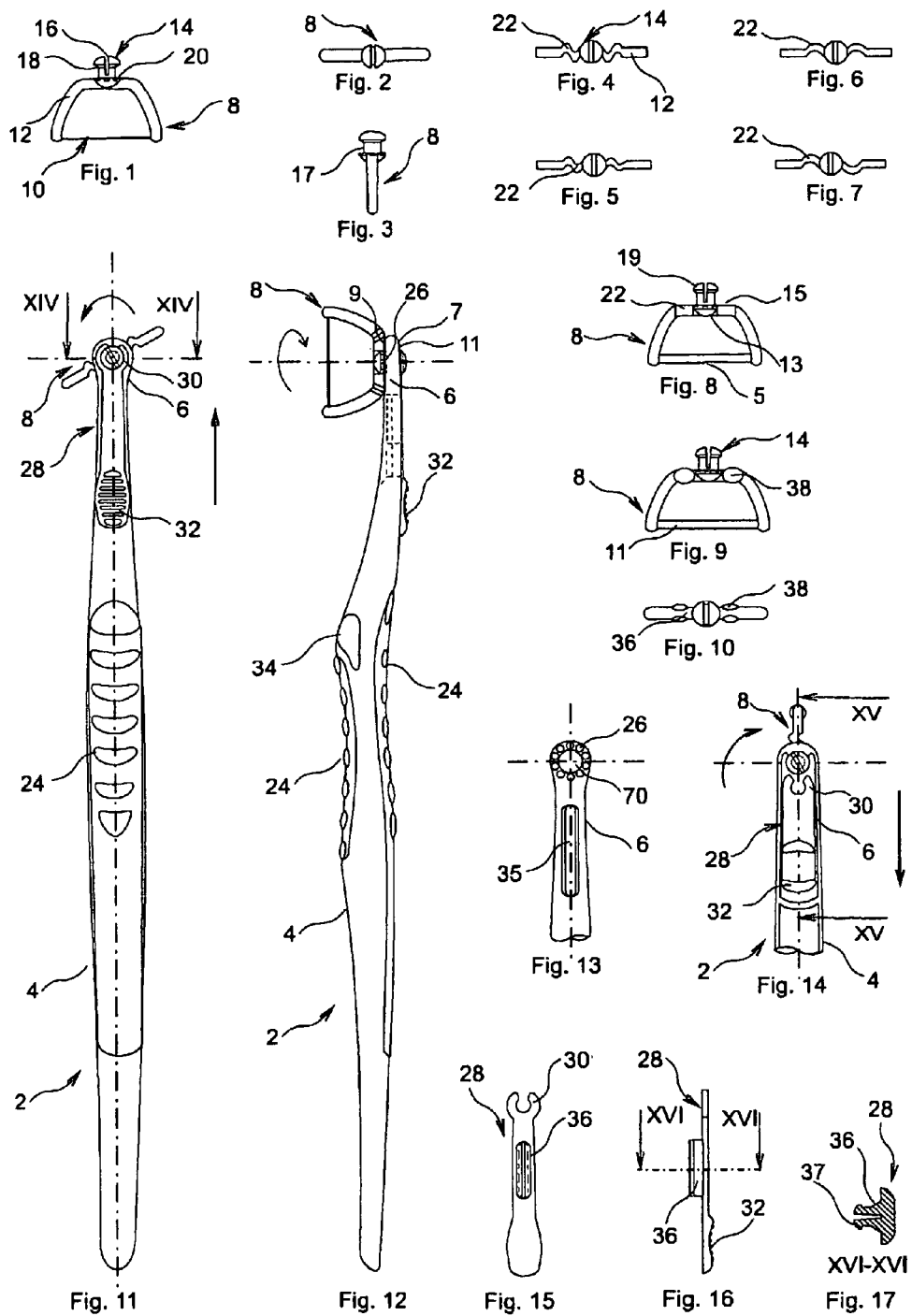

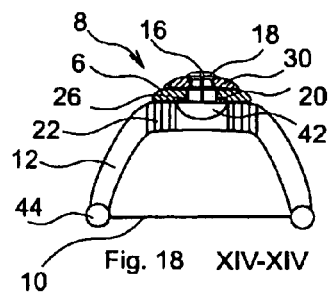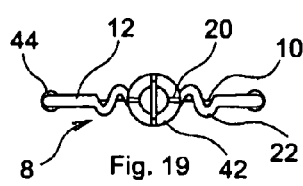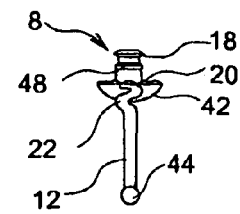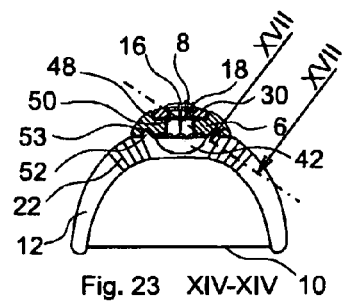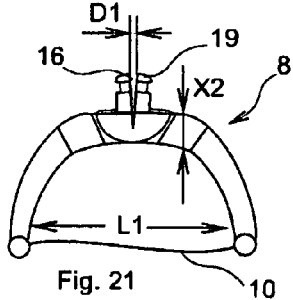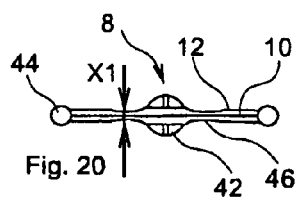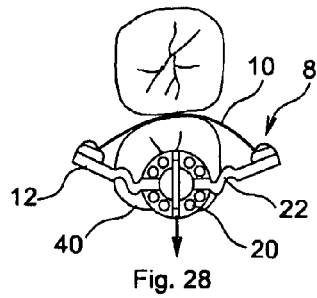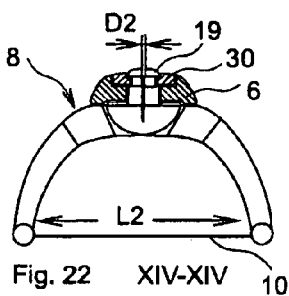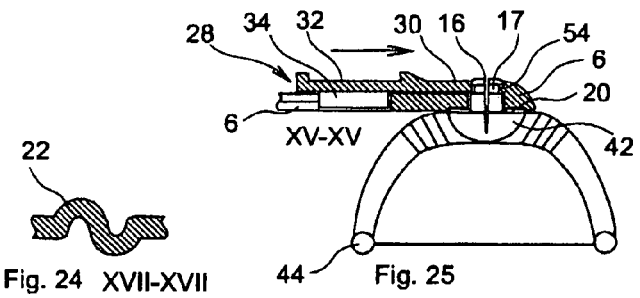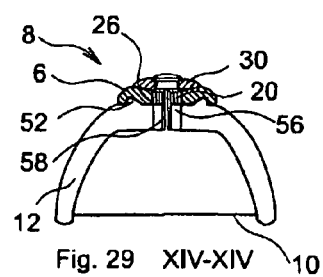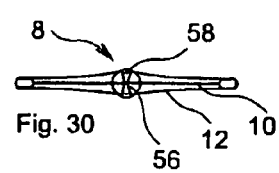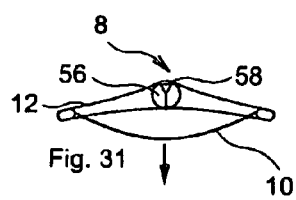

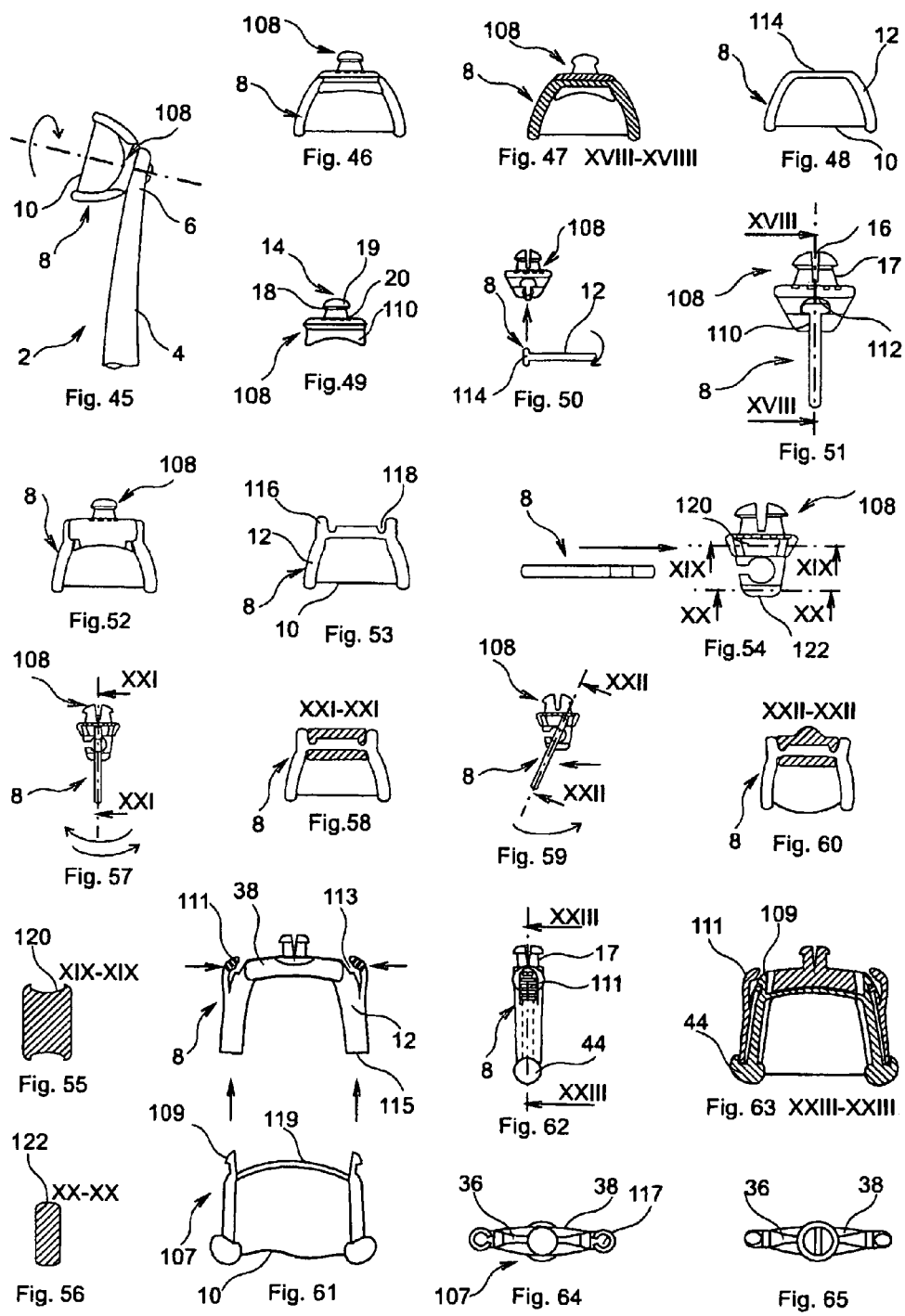

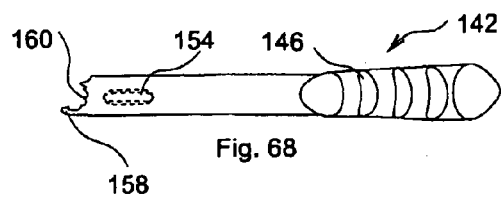
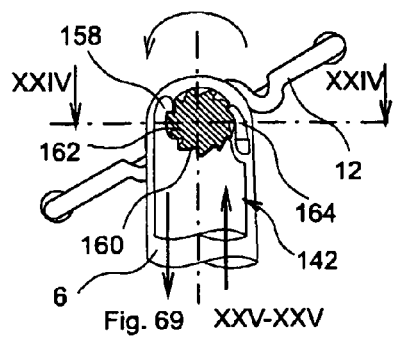
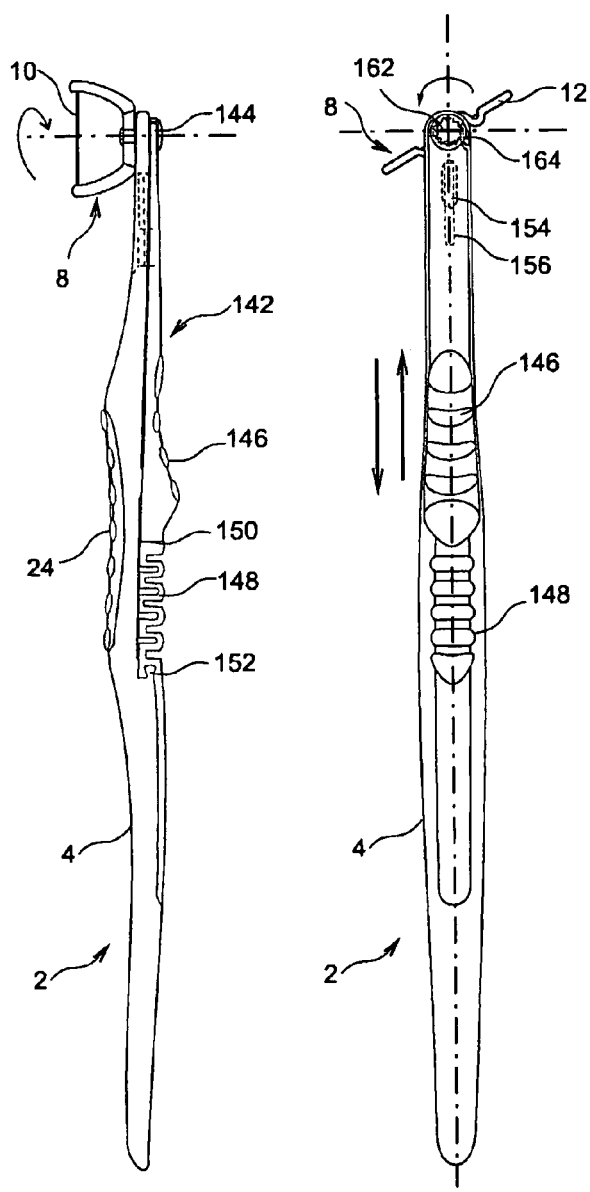
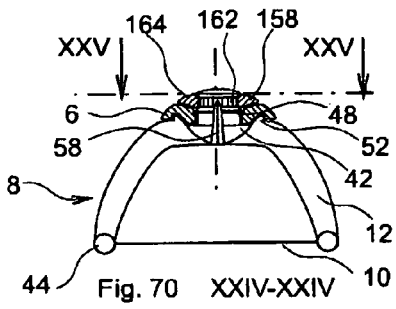
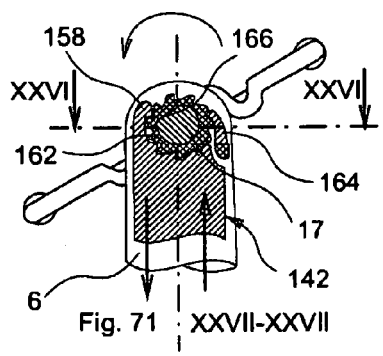
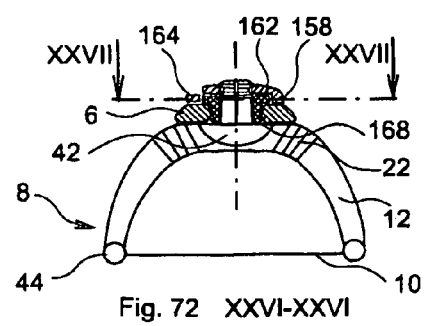

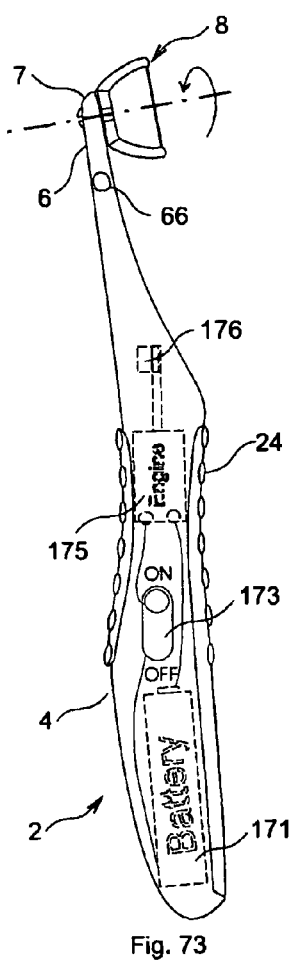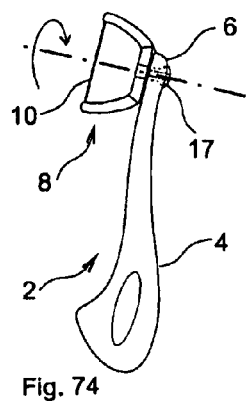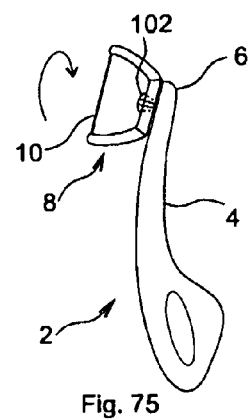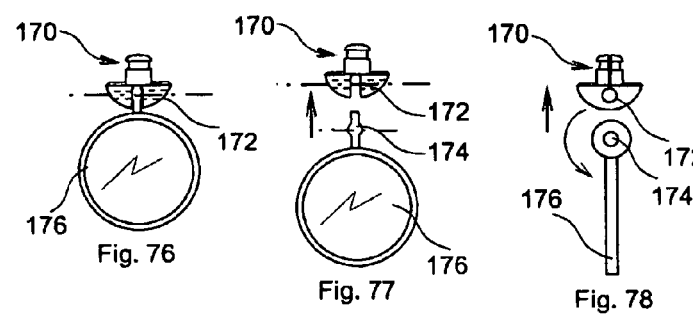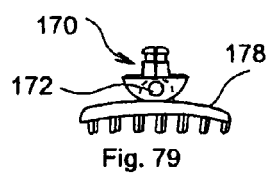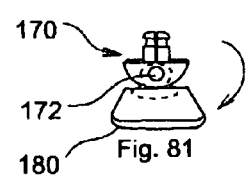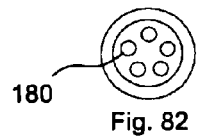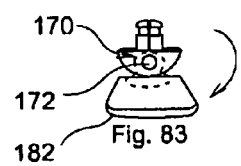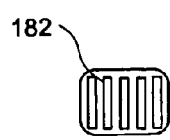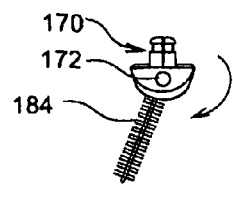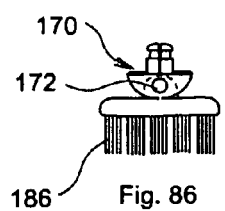

ERGONOMIC DENTAL FLOSSING DEVICE

RELATED APPLICATION

This application claims the benefit of priority to PCT application No. PCT/IL2005/00124, filed Nov. 23, 2005, which in turn claims the benefit of priority to U.S. provisional applications No. 60/630,462 filed Nov. 24, 2004, and 60/670,275, filed Apr. 12, 2005. The above mentioned applications are incorporated herein by reference in their entirety.

FIELD OF THE INVENTION

The present invention relates to the field of dental flossing devices with adjustable floss holders, especially of types designed to provide cleaning of additional surfaces of the teeth, not limited to the interdental spaces.

BACKGROUND OF THE INVENTION

Flossing devices of various kinds are known in the art. For example, U.S. Utility Pat. No. 664,126 describes a simple floss holder aligned with the grasping means, U.S. Utility Pat. No. 5,483,982 shows a disposable floss holder bow perpendicular with the grasping means, and U.S. Utility Pat. No. 3,927,686 discloses a swiveling head disposable bow on a grasping means. Other kinds, such as different types of bows held on different type of handles or even combined with a toothbrush are also known.

The above-mentioned flossing devices do not satisfactorily fulfill their task. The known manually operated bow-type flossers, because they have the dental floss either aligned or perpendicular with the handle, are difficult to operate when trying to clean the back teeth or front teeth because of the inappropriate orientation of the floss string. Other bow-type devices do not have the appropriate means for securing the bow on the handle. Another shortcoming of all of these prior art bow-type flossers is that the tension in the flossing string is fixed, so that the relatively high tension required to enable proper insertion of the floss between the teeth, which action requires the floss to remain tense, does not allow the floss to curve around the profile of the teeth away from the interdental space. As a consequence, proper cleaning of plaque and bacteria from surfaces of the teeth other than interdental surfaces is not readily performed. Furthermore, the high tension of the floss in prior art flossers presents a danger of easily wounding the delicate tissue of the gums when attempting to clean surfaces of the teeth other than the interdental spaces.

The disclosures of each of the publications mentioned in this section and in other sections of the specification are hereby incorporated by reference, each in its entirety.

SUMMARY OF THE INVENTION

The present invention seeks to provide a new flossing device having an optimized ergonomic structure, with a swiveling head that can be easily adjusted in several positions for optimal reach between any pair of teeth in the mouth, and the means for easy adjustment of tension in the flossing string, that enables an appropriate level of tension for each type of action performed when flossing. The special geometry of the floss head allows the floss string tension to adjust only when needed, which is when the floss holder head is pushed against the sides of the teeth in a lateral movement, allowing the dental floss to adhere to the contour of the teeth during the flossing operation, for optimized cleaning and to avoid wounding the delicate tissue of the gums at the base of the teeth.

It is a further object of the present invention to provide a flossing device with improved ergonomic features, providing higher safety standards and having improved cleaning capability and efficiency.

In accordance with a first preferred embodiment of the present invention, there is therefore provided a flossing device which is comprised of a floss holder, comprising a base, a pair of spaced-apart arms that extend in a "C" shape from the base, which secure one two or more lengths of dental floss at their tips, configured to be moved between the teeth, while positioned inside the oral cavity. The floss holder has its base anchored in a fixed permanent or in a replaceable way with an easy locking mechanism onto the head portion of a grasping means, such that it can swivel around the axis of the base, and can be adjusted in several positions by means of a complementary set of interlocking protrusions and depressions at the contact surface between the floss holder and the head portion of the grasping means; alternatively the floss holder has a mechanism for controlling the tension in the dental floss such that it is maximal before and during the insertion in between the teeth and is less taut when the floss is between the teeth and is pushed from the base in a lateral motion against the sides of the teeth, in order to allow it to adhere optimally to the contour of the teeth during the flossing operation. This is achieved by providing the floss holder with anisotropic flexibility, such that it has more flexibility in a direction laterally perpendicular to the floss, than it has in the direction perpendicular to the floss; orthogonal to the lateral direction. The direction laterally perpendicular to the floss is understood throughout this application, and is thus claimed, to mean the direction generally perpendicular to the floss, and in the plane of the row of teeth being flossed, i.e. generally horizontally, while the direction orthogonal thereto is understood to mean the direction generally perpendicular to the floss, and generally out of the plane of the subject's row of teeth, i.e. generally vertically.

According to one preferred embodiment of the present invention, this anisotropic flexibility is preferably achieved by constructing at least part of the base or the arms of the floss holder bow such that their dimension laterally perpendicular to the direction of the floss, is thinner than their dimension parallel to the direction of the floss. Thus, the thicker dimension maintains the floss in a state of tension while the floss is being pushed down between the teeth, and while the floss is being pushed to and fro between the teeth, but the additional flexure in the direction laterally perpendicular to the floss, provided by the thinner section of the support arms in that direction, enables the floss arms to bend round the tooth profile when such lateral pressure is applied to the tooth.

According to another preferred embodiment of the present invention, this anisotropic flexibility is preferably achieved by constructing the base of the arms of the floss holder bow with a convoluted section, such as in the form of an "S", oriented in such a direction that additional flexibility is provided to the arms in the direction laterally perpendicular to the floss.

According to a third preferred mechanism, this anisotropic flexibility is preferably assisted by constructing a profiled slit in the head post of the floss holder bow, by which it is attached to the flosser handle, the slit being shaped such that it enables the floss holder bow to bend in the direction laterally perpendicular to the floss, as the floss is tensioned in that direction.

The extent of the floss bow bending is limited by contact between the two edges of the slit, thereby preventing further bending in that plane.

According to a fourth preferred embodiment, in addition to the said anisotropic flexibility in the base of the floss head, elasticity is preferably achieved by coating the base of the arms of the floss holder bow with a more flexible material than the arms, such that the floss bow can bend in the direction laterally perpendicular to the floss as the floss is tensioned in that direction and more easily return to its former position over the course of repeated uses.

The head portion is attached in a permanent or replaceable fashion, such as by swiveling, to the grasping means through a clipping mechanism. Means are also provided for grasping the head and imparting controlled movements between the teeth.

There is therefore provided in accordance with a preferred embodiment of the present invention, a dental flossing device comprising a handle having a head portion and a grasping portion, and a floss holder attached to the head portion, the floss holder comprising a base portion and a pair of spaced-apart arms projecting from the base portion and accommodating at least one length of dental floss therebetween, wherein the floss holder has greater flexibility in a direction laterally perpendicular to the direction of the length of dental floss than in the direction of the floss itself. In this dental flossing device, at least one of the base portion and the pair of spaced-apart arms of the floss holder preferably comprises at least one convoluted section, such that the floss holder arms have greater flexibility in a direction laterally perpendicular to the direction of the length of dental floss than in the direction of the floss itself.

Alternatively and preferably, at least one of the base portion and the pair of spaced-apart arms of the floss holder has a reduced cross sectional dimension in the lateral direction generally perpendicular to the floss than its cross sectional dimension in the direction generally parallel to the floss, such that the floss holder arms have greater flexibility in a direction laterally perpendicular to the direction of the length of dental floss than in the direction of the floss itself.

There is further provided in accordance with yet another preferred embodiment of the present invention, a dental flossing device as described above, and wherein at least one of the base portion and the pair of spaced-apart arms of the floss holder is coated with a material more elastic than that of the arms in order to add elasticity to the arms of the floss holder in a direction laterally perpendicular to the direction of the length of floss.

In any of the above-described embodiments, the floss holder base portion is preferably attached to the head portion of the handle by means of an opening in the base portion and engaged onto a neck projecting from the head portion. Alternatively, the floss holder base portion is preferably attached to the head portion of the handle by means of a neck protruding from the base portion and engaged in a sleeve in the head portion. In such a case, the neck preferably has a groove along at least part of its length, the groove being aligned in a direction generally perpendicular to the direction of the floss, such that the floss holder arms have greater flexibility in a direction laterally perpendicular to the direction of the length of dental floss than in the direction of the floss itself.

In accordance with still another preferred embodiment of the present invention, there is provided a dental flossing device comprising a handle having a head portion and a grasping portion, and a floss holder attached to the head portion, the floss holder comprising a neck, a base portion and a pair of spaced-apart arms projecting from the base portion and accommodating at least one length of dental floss therebetween, wherein the floss holder has a groove in the neck, so that when the neck is inserted into a hole in the head portion, the groove is compressed, such that the arms of the floss holder are extended thereby increasing dental floss tension.

There is further provided in accordance with still another preferred embodiment of the present invention, a dental flossing device comprising a handle having a head portion with an opening, a grasping portion, and a floss holder attached to the head portion, the floss holder comprising a neck, a base portion and a pair of spaced-apart arms projecting from the base portion and accommodating at least one length of dental floss therebetween, wherein the floss handle has at least one protruding ridge into the opening designed to engage grooves on the neck portion of the floss head which retain the floss holder in a position for securing by the grasping means.

There is further provided in accordance with still another preferred embodiment of the present invention, a dental flossing device comprising a handle having a head portion, a grasping portion, and a floss holder attached to the head portion, the floss holder comprising a neck, a base portion and a pair of spaced-apart arms projecting from the base portion and accommodating at least one length of dental floss therebetween, wherein the floss holder has an upper face with a central area having a shoulder reinforcement enabling the head portion to be anchored to the head portion, preventing undesired lateral looseness of the floss holder head when the floss is under lateral stress.

There is further provided in accordance with yet another preferred embodiment of the present invention, a dental flossing device as described above, wherein a groove in the neck of the floss holder has opposing faces which limit the bending motion of the floss holder arms in a direction laterally perpendicular to the length of dental floss.

In any of the above-described embodiments, the floss holder base portion is preferably attached to the head piece of the handle by means of an opening in the base portion and engaged onto a neck projecting from the floss holder and is demountably attached to the head portion of the handle.

In any of the above-described embodiments, the at least one length of dental floss may preferably be two lengths of dental floss.

In any of the above-described embodiments, the floss holder neck portion is allowed to be attached onto or detached from the head portion and secured with the locking means only when the groove in the tip is oriented in a preset direction.

In any of the above-described embodiments, the floss holder is attached to the head by means of clipping into a groove on an intermediary holder.

There is further provided in accordance with yet another preferred embodiment of the present invention, a dental flossing device having a floss holder with a neck, as described above wherein the neck of the floss holder comprises a step advancement mechanism via a unidirectional toothed wheel which is activated with a hooked slider on the head piece which changes the angle of the floss holder.

In any of the above-described embodiments, the floss holder base portion is preferably attached to the head which is attached to the grasping portion allowing it to rotate around its own axis through a preset number of positions.

In any of the above-described embodiments, the floss holder base portion may preferably be attached to the head portion by means of an intermediate holder which has a groove with a thinner opening on the upper side allowing it to interlock with the floss holder arms and secure it in the floss holder base.

In any of the above-described embodiments, the floss holder base portion is preferably attached to the head through an intermediate holder which has a groggy and a thinner opening on the front side which interlocks with the floss holder arms and secures it inside and wherein the intermediate holder also adjusts the tension in the dental floss string during use due to extensions of the floss holder arms which follow concave surfaces on the lateral walls of the intermediary holder and push the tips of the arms towards each other.

In any of the above-described embodiments, the grasping portion may preferably be constructed to include an electromechanical vibrator.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the details shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

In the drawings:

FIGS. 1, 2 and 3 are respectively front, bottom and side views of the floss holder;

FIGS. 4, 5, 6, 7 and 8 are respectively bottom and front views of a different embodiment of the floss holder 8, having wavy zones in the base area for enhanced lateral flexibility;

FIGS. 9 and 10 are respectively front and bottom views of a different embodiment of the floss holder 8 with double string, having at the base level a thinner area covered with elastomer insertion for enhanced side flexibility;

FIGS. 11 and 12 are respectively back and side views of the flossing device with swiveling head, showing the sliding lock in secured position;

FIG. 13 is a front cut view of the flossing device with the sliding lock disassembled;

FIG. 14 is a back view of the flossing device, with a recessed sliding lock in open position;

FIGS. 15, 16 and 17 are respectively bottom, side and sectional views of a sliding lock.

FIGS. 18 and 19 are a front and respectively bottom views of the floss holder having a convoluted shape for lateral flexibility, and with a cross-sectional view XIV-XIV through the head portion and slider lock from FIG. 11;

FIG. 20 is a top view of an embodiment of the floss holder, 8 having a thinner area in the base area for enhanced lateral flexibility;

FIGS. 21 and 22 are a front view of the floss holder, with dental floss string relaxed, before and respectively after being assembled and secured into the opening in the head portion of the handle, when the string becomes tensed due to compressing the slit in the post of the floss holder;

FIG. 23 is a front view of the floss holder with a cross-sectional XIV-XIV view of the floss device from FIG. 11, where the sliding lock is recessed into the head portion, with angled convoluted shape for lateral flexibility, and special wings for reduced vertical flexibility, and additional protruding edge for securing the floss holder in place;

Figure 32:
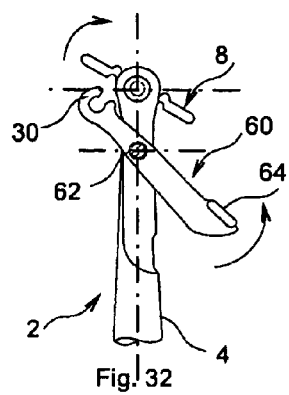
Figure 33:
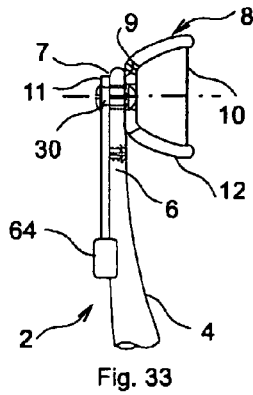
Figure 34:
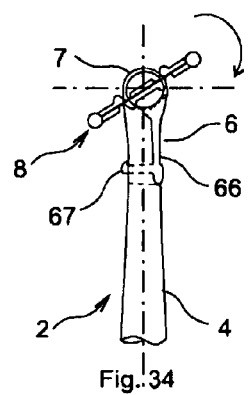
Figure 36:
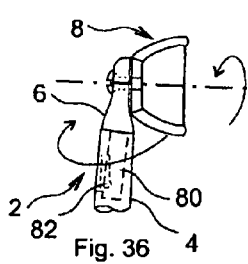
Figure 37:
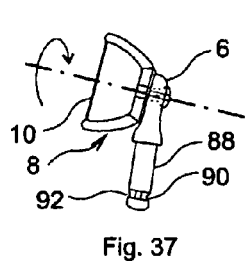
Figure 35:
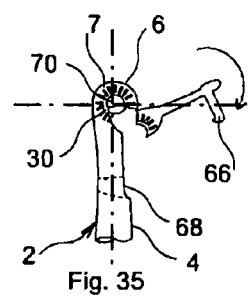
Figure 38:
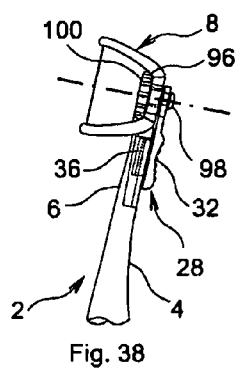
Figure 39:
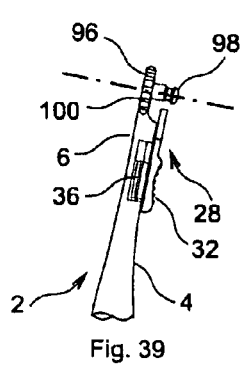
Figure 40:
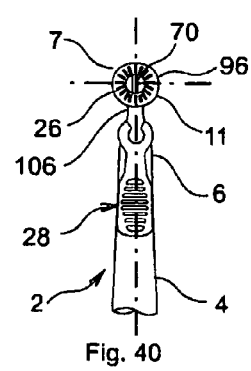
Figure 41:
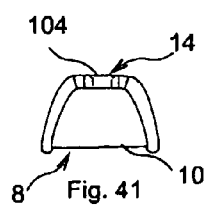
Figure 42:
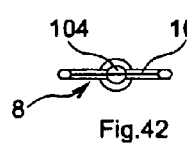
Figure 43:
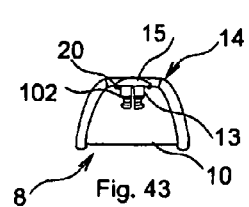
Figure 44:
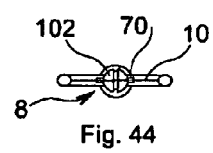

FIG. 24 is a cross-sectional XVII-XVII view through the wavy area seen in FIG. 23;

FIG. 25 is a front view of the floss holder with a longitudinal-sectional view XV-XV through the head portion and the sliding lock from FIG. 14, where the head portion opening has a special protrusion designed for trapping the neck (Post) of the floss holder in the correct position to enable securing it with the sliding lock;

FIGS. 26, 27 and 28 are side and top views of the floss holder in relaxed position and respectively under stress during work, showing the bent arms of the floss holder and the string following the natural contour of the tooth;

FIGS. 29, 30 and 31 are front and respectively top views of a floss holder with a torsion lateral flexibility mechanism, with cross-sectional XIV-XIV views from FIG. 11;

FIGS. 32 and 33 are back and respectively side cut views of the flossing device where the floss holder is secured in the head portion through the use of a swinging lock;

FIGS. 34 and 35 are top views of the flossing device with swiveling head, with a lateral lock for the swinging floss holder in respectively secured and opened position;

FIG. 36 is a side view of the flossing device where the head portion is connected in a replaceable or permanent, swiveling fashion to the grasping means of the flossing device;

FIG. 37 is the side view of the head portion from FIG. 36 with a floss holder assembled, FIGS. 38 and 39 are side views of a flossing device that has a projection in the head portion, with a mounted and respectively un-mounted swiveling floss holder from the lower side of said head portion, and secured with a sliding lock mechanism;

FIG. 40 is a back view of the flossing device handle from FIG. 38, with a thinner neck area to enable maximum swiveling freedom for the floss holder;

FIGS. 41 and 42 are respectively side and top views of a floss holder with a securing penetration in the base, designed for the device from FIG. 38;

FIGS. 43 and 44 are respectively side and top views of a floss holder with a securing projection on the upper side of the base, designed for a variation of device from FIG. 38 not seen here where the head portion has a matching opening to attach this floss holder;

FIG. 45 is a side view of the flossing device with an intermediary holder;

FIGS. 46 and 47 are respectively front view of the floss holder assembled in the intermediary holder, and a cross section through them;

FIG. 48 is a front view of the floss holder designed for the intermediary holder.

FIG. 49 is a front view of the intermediary holder for the floss holder;

FIG. 50 is a side view of the intermediary holder, showing the assembling method;

FIG. 51 is a side view of the floss holder assembled in the intermediary holder;

FIG. 52 is a front view of an intermediary holder with the floss holder assembled;

FIG. 53 is a front view of a floss holder seen mounted in FIG. 52;

FIG. 54 is a lateral view showing the side assembly method of the floss holder into the intermediary holder, which allows a limited swinging movement of the floss holder;

FIG. 55 is a XIX-XIX sectional view through the intermediary holder from FIG. 54;

FIG. 56 is a XX-XX sectional view through the intermediary holder from FIG. 54;

FIG. 57 is a side view of the intermediary holder from FIG. 52, with floss holder relaxed;

FIG. 58 is a sectional XXI-XXI front view of the intermediary holder from FIG. 57, with the floss holder mounted, which enables full tension in the flossing string;

FIG. 59 is a side view of the intermediary holder from FIG. 52, with the floss holder mounted and which is under lateral stress;

FIG. 60 is a sectional XXII-XXII front view of the intermediary holder from FIG. 59, where the arms of the floss holder bend closer to each other and release tension of the floss;

FIG. 61 is a front view of a swiveling intermediary holder endowed with anisotropic lateral flexibility and higher elasticity, designed to engage with a thinner floss holder;

FIG. 62 is a side view of the intermediary holder;

FIG. 63 is a XXIII-XXIII cross section through the intermediary holder and floss holder;

FIGS. 64 and 65 are top and respectively bottom views of the intermediary holder.

FIGS. 66 and 67 are respectively side and bottom views of a flossing device with a sliding mechanism for controlled step by step rotational advancement of the floss holder;

FIG. 68 is a front view of the slider from the advancement mechanism in FIG. 66;

FIG. 69 is an enlarged view of the advancement mechanism, with a XXV-XXV cross-sectional view through the toothed-wheel, which is part of the floss holder;

FIG. 70 is a front view of a floss holder from FIG. 69 that has a torsion lateral flexibility mechanism, with a XXIV-XXIV cross-sectional view through said advancement mechanism;

FIG. 71 is an enlarged XXVII-XXVII cross-sectional view through the advancement mechanism, from the bottom of the flossing device, where toothed-wheel is a separate element, and it rotates synchronically with floss holder;

FIG. 72 is a front view of the floss holder from FIG. 71, with convoluted shapes on the arms for enhanced lateral flexibility, and with a XXVI-XXVI cross-sectional view;

FIG. 73 is a dental floss device where the swiveling floss holder endowed with lateral flexibility is mounted on an electromechanical or electronic vibrating handle.

FIGS. 74 and 75 are two embodiments of disposable dental floss devices;

FIGS. 76, 79, 81, 83, 85 and 86 are side views of respectively an oral mirror, tongue cleaner, gum massager, plaque remover, interdental brush, and tooth brush heads enabled to be attached in a swinging or fixed manner to a swiveling intermediary holder base, that can be secured to the head portions of any of the previously seen handles;

FIGS. 77 and 78 are front and side views of the mirror and intermediary holder base;

FIG. 80 is a top view of a tongue cleaner;

FIG. 82 is a top view of the gum massager, and

FIG. 84 is a top view of a plaque remover.

DETAILED DESCRIPTION OF PREFERRED EMBODIMENTS

Referring now to the drawings, there is illustrated in FIGS. 11, 12 and 13 a preferred embodiment of the flossing device, 2 according to the present invention.

The flossing device essentially comprises two parts: a head portion, 6 and a grasping means, 4, which may be made of any suitable material such as plastic, as an integral unit or as two separate, detachable inter-connectable units, rendering the head portion disposable after one or more uses. The finger grips, 24 on the grasping means can be made out of the same material as the grasping means or out of elastomer material. The sole purpose of the grasping means is to hold and manually move the head portion with the floss holder mounted on it in between the teeth, in a straight, and/or circular motion, while applying controlled pressure. Hence, while the most commonly used grasping means is embodied by a handle of any kind, including those of the type employed with a toothbrush, other types of handles or grasping means could just as well be used. For example, instead of a handle, the head portion 6 may be provided with curved side recesses (not shown), so that it may be gripped by two fingers, or with a loop or other such means for engaging one finger, to effect the reciprocating movements of the device along the surfaces between the teeth.

The head portion 6 comprises a base 7 having an upper face 9 and a lower face 11, has a means of securing the floss holder onto this base that may be embodied by a sliding locking fork 28 as in FIGS. 11 and 14 or as a swinging locking fork as in FIGS. 32 and 34.

As seen in FIG. 13 the base, 7 is endowed with a perforation, 70 and several depressions, 26 for interlocking with the protrusions, 20 on the floss holder, 8, to allow the last one swivel through several predefined positions, when mounted on the head portion, in order to adjust the most convenient angle of the floss holder during use. The floss holder, 8 in FIGS. 1, 2, 3 and 8 has a base, 14 that has an upper face, 13 and a lower face, 15, and a pair of arms, 12 which extend from this base in a "U" shape on the upper face, 13 to secure a length of dental floss, 10 in between their tips, or a double dental floss, 5 as seen in FIG. 4. The base, 14 has a means to mount the floss holder, 8 onto the base, 7 of the head portion, 6 which is embodied in FIGS. 1 and 3 as a neck portion, 17 that extends from the lower face, 15 of the base 14. This neck, 17 has a transversal slit, 16 and a larger tip, 19 that has a tapered undercut, 18 on the neck side, to enable a fit anchoring into the specially designed perforation, 70 of the head portion, 6. When the floss holder is assembled with its neck, 17 inserted into the perforation, 70 of the head portion, the slit 16 is compressed, the two sections of the tip, 19, are drawn closer together, thereby providing additional tension in the arms of the floss holder; it is also provided with several protrusions, 20 that are meant to interlock with the depressions, 26 from the upper face, 9 of the base, 7 of the head portion, 6.

In an alternative embodiment of the floss holder in FIGS. 8 and 4, the arms are endowed near the base area, 14 with a convoluted section, 22 preferably having an "S" shape, or any similar wavy shape which provides enhanced lateral flexibility of the arms, 12 in the direction generally perpendicular to the floss and to the neck 17. The arms can thus bend closer to each other, as seen in FIGS. 27 and 28, when lateral pressure is applied from the base, 14 on the dental floss, 10 against the tooth 40, during the cleaning of the sides of the teeth other than inside the interdental space. This convoluted section 22 enables tension adjustment in the dental floss string when required, to enable maximal contact with the side contours of the teeth, 40 not immediately facing the interdental gap, without wounding the delicate tissue of the gums between the teeth. This specially designed lateral flexibility does not affect the initial maximal tension of the dental floss, 10 needed when stress is applied in a vertical direction, when inserting the floss, 10 in between the teeth, 40 and extracting it again.

Reference is now made to FIG. 29, which is a further preferred embodiment for providing the desired lateral flexibility of the floss holder, 8 using a torsion side flexibility mechanism. The floss holder has two longitudinal radial deep grooves, 58 along the reinforcement, 56 along the axis of the floss holder, one on each lateral side of the axis at the base level. These grooves continue towards the lower face of the floss holder. When lateral stress is applied on the dental floss, 10, the floss holder will preferably bend near the root of the rod, due to the torsion flexibility along the longitudinal reinforcements 56. The faces of the opening of the grooves are not parallel, each face having a negative chamfer, as shown in FIG. 30. The bending of the floss holder will be limited by the meeting of the faces of the opening of the grooves, 58 as seen in FIG. 31. FIG. 30 thus shows the arms, 12 in a relaxed state and FIG. 31 shows the arms when under lateral stress. In order to keep the floss holder in a preferred angular position, a set of interlocking protrusions, 20 and depressions, 20 are provided on the neck, 17 of the floss holder, and respectively, 26 on the head portion, 6.

Reference is now made to FIGS. 20 and 21, in which is shown a further preferred embodiment for providing the desired lateral flexibility of the floss holder 8, by constructing the arms, 12 such that their cross section in the area, 46 near the neck, 17 of the holder is not uniform in both orthogonal directions, but has a thinner dimension, X1 in the lateral direction generally perpendicular to the floss than the dimension, X2 (seen in FIG. 21) in the direction generally parallel to the floss. Thus, the thicker dimension maintains the floss in a state of tension while the floss is being pushed down, and extracted from between the teeth, but the additional flexure in the direction laterally perpendicular to the floss, provided by the thinner dimension of the support arms in that direction, enables the floss, 10 to bend round the tooth profile, 41 when such lateral pressure is applied to the tooth, 40.

An enhancement to this design is seen in FIGS. 9 and 10 where the thinner areas 36 are covered with elastomer, 38 that bonds to these areas in order to provide higher elasticity to the In FIG. 11 there is shown a back view of the flossing device, 2 with the floss holder, 8 mounted on the head portion, 6, and secured in its working state so that it can be rotated through a number of preset positions. In this case the sliding lock, 28 is in closed position after being pushed with a finger from the grip, 32 towards the head portion of the device, and when the fork, 30 present at its tip hugs the neck, 17 of the floss holder, 8.

FIG. 14 displays a similar flossing device similar to the in from FIG. 11 where the recessed sliding lock, 28 is in its open position, pulled away from the floss holder, and when the fork, 30 has been disengaged from the neck, 17 of the floss holder, therefore releasing it.

In FIG. 13 a front view is shown of the same flossing device in FIG. 11, where the sliding lock, 28 is not assembled. On the ring around the opening, 70 there are several depressions, 26 meant to interlock with two or more protrusions, 20 on the lower side of the base 15, of the floss holder, 8. Once the floss holder, 8 is locked and secured in working position at a certain preferred angle, the interlocking will be strong enough to keep this orientation and prevent the floss holder from rotating during use, even under the stress implied by exercising the lateral flexibility, when the arms, 12 of the floss holder repeatedly bend and hug the teeth, as seen in FIGS. 27 and 28.

When stronger force is manually applied on the floss holder, 8 it will jump to the next angular preset position and therefore be secured for the following preferred working position, best for cleaning between another pair of teeth.

In FIG. 12 there is disclosed a side view of the preferred embodiment of FIG. 11, where the ergonomic design of the handle, 4 is shown, with elastomer finger grips, 24 and additional grips, 34 for an alternative way of holding the handle while in use, like a pen.

FIG. 15 shows a back view of the locking slider, 28, where the fork, 30 seen at its tip is designed to be flexible enough to clip easily, hug the neck, 17 of the floss holder, and keep it secured to the head portion 6.

FIG. 17 is a XVI-XVI cross-sectional view through the slider, where we see the clipping extension, 36 that enables the edges, 37 to snap in and laterally fit into the sliding channel, 35, seen in FIG. 13.

FIG. 18 shows an enlarged view of the floss holder, 8 where it can be seen in a XIV-XIV cross-sectional view through the device from FIG. 11, the manner in which it is assembled onto the head portion, 6 and locked in its working state with the help of the fork, 30 of the sliding lock, 28. There is a shoulder, present at the lower side of the base of the floss holder, 8 to prevent loose movement and rattling inside the perforation 70 through the head portion, while the product is in use and the floss holder is under lateral stress. The protrusions, 20 can also be seen, interlocking with complementary depressions, 26 present on the upper face, 9 of the head portion. The slit, 16 through the neck, 17 of the floss holder, and the angular undercuts, 18 on the sides of the neck are designed to enable a fit anchoring into the perforation, 70 of the head portion and also allow a certain degree of longitudinal elastic fit needed to resist the stress along the neck 17 of the floss holder, generated when being rotated to the next preferred working angle.

In FIG. 19, there is clearly seen the wavy shaped base rod, 22 designed for enhancing the lateral flexibility of the floss holder, enabling the tips 6f the arms, 12 to come closer to each other easier, allow the floss to hug the teeth and follow the natural side contour of the teeth.

This type of preferred lateral bending occurs when the device is in use and pressure is applied on the dental floss against the sides of the teeth, 40 while cleaning up and down their sides 41, as seen in FIGS. 27, and 28. Also for safety reasons use is made of rounded ends, 44 at the tips of the arms, 12 of the floss holder.

FIG. 23 presents a similar floss holder as in FIG. 18, but with a pair of wing shaped protrusions, 52 present on the lower face, 15 of the base 14 of the floss holder designed to interlock radial into a complementary circular groove, 53 present on the upper face, 9 of the head portion, 6, for the purpose of preventing the tips of the arms, 12 to bend closer to each other when vertical stress is applied onto the floss holder, when the dental floss is inserted and extracted from the interdental space.

In addition, this floss holder has the wavy profile, 22 present along the arms 12, in the zone where the arms are inclined at any angle greater than 0 and less than 90 degrees against the symmetrical axis of the floss holder, preferably in the zone closer to the base of the arms, where the angles are around 45 degrees. In this way, during use, when lateral stress is exerted against the dental floss, the arms, 12 will have this area 22, as an enhanced preferred bending zone, which brings the tips of the arms closer to each other, allowing the floss to hug the teeth, and therefore adjusting the tension the dental floss for optimal contact against the sides of the teeth. Also as can be seen in the cross-sectional XIV-XIV the sliding lock, 28 and with the fork, 30 are recessed into the head portion, 6, for ergonomic reasons. An additional enhancement, that can be seen as well in FIG. 26, embodied into a protruded edge, 48 is present on the neck, 17 of the floss holder, designed to hold the neck, 17 through a clipping mechanism in the correct vertical position ready to be locked and secured in its working position with the sliding lock 28, for a smooth safe and easy slide locking operation. The said clipping mechanism is against the circular internal groove, 50 present in the opening, 70 of the head portion.

In FIG. 24, there is shown an inclined sectional XVII-XVII view along one of the arms, 12, of floss holder in FIG. 23 that displays the "S" shape of the arms in this embodiment. FIGS. 21 and respectively 22 show the embedded mechanism for enhancing the tension in the dental floss between the arms, 12 due to the opened slit, 16, of width D2, present in the neck, 17, which becomes compressed to a width D2 smaller than D2, when inserted and secured in working position in the opening, 70 in the head portion, 6, therefore moving the tips of the arms, 12 apart form each other, from an initial width L1 to higher final one L2 when assembled.

FIG. 25 shows a longitudinal sectional XV-XV view through the device form FIG. 14, the mechanism for trapping the neck, 17 of the floss holder, 8 in the opening, 70 in the head portion 6, through the use of a specially designed protrusion, 54, present on the inside wall of the said opening, 70 that allows the tip, 19 of the neck to clip over the protrusion, 54, and therefore have the neck of the floss holder in "ready to lock" correct position to activate the sliding lock, 28 when the fork, 30 secures the floss holder in working position. The neck of the floss holder can be inserted only when the slit, 16 is substantially aligned parallel to the said protrusion, 54 and is slightly compressed when neck is clipped inside the opening.

FIGS. 26, 27, and 28 show two lateral views, and a bottom view of the floss holder, in a relaxed state, and respectively under stress, where the preferred lateral flexibility mechanism operation can be seen, with the arms, 12 bending in the desired zones, the floss hugging the teeth, and the rounded tips, 44 closer to each other to enable the dental floss enhanced contact and cleaning of the side of the teeth.

In FIG. 32 is presented a bottom view of the flossing device with a swinging locking mechanism, 60 which, displayed in open state, can rotate around a bolt, 62, present in the middle zone of the swinging lock, and which clips into a perforation in the head portion. The swinging lock, 60 has at its tip a fork 30, with a lateral opening meant to snap fit onto the neck area, 17 of the floss holder, when last one secured in working position.

In FIG. 34 the swinging locking arm, 66 is designed to allow its end part 67 to slide and lock inside a perforation, 68 in the head portion, 6, seen in FIG. 35, in order to secure the floss holder in working position.

FIG. 36 discloses an embodiment of the flossing device where head portion, 6 is attached onto the tip of the grasping means, and allow the head portion comprising the swiveling floss holder to rotate around its own axis through several preset positions, therefore enabling the user to adjust the head portion to the most convenient angle for use.

In FIG. 37 is seen a side view of a head portion 6, which ends with a rod, 88 that has a thinner area, 90 for the clipping mechanism. Said rod is anchored into a specially designed sleeve, 80 present on the tip of the grasping means. Said thinner area 90 is covered with a set of grooves, 92 for adjusting the rotation angle of the head portion 6, through a number of positions. Onto the inside wall of the sleeve 80, shown in FIG. 36 there is a clipping protrusion, 82 designed to interlock with the area, 92 of said rod, 88.

In FIG. 38, the detachable floss holder seen in FIG. 41 has a perforation, 104 on its base, 14 for getting anchored onto the clipping projection, 98 present on the lower face, 11 of the disk-like base, 96 at the tip of the head portion 6. The floss holder 8 from FIG. 41 has its arms, 12 embracing the disk 96, from its lower face 11, so that it can swivel through several preset positions due to a set of grooves, 100 built on the periphery of the disk, 96 that interlock with interior sides of the arms. The floss head, 8 is secured to the head portion using a sliding lock, 28 present on the lower side of the head portion.

In FIG. 40 there can be seen the area, 106 of the head portion near the disk, 96 and which is narrower in order to enable the floss holder maximal swiveling freedom.

In FIG. 45 the head portion, 6 of the flossing device, 2 has attached an intermediary holder part, 108, that can swivel through several preset positions. The intermediary holder, 108 has a clipping protrusion, 17 seen in FIG. 49 which allows it to be anchored in a swiveling fashion onto the base, 7 of the head portion of the grasping means.

AS seen in FIG. 51, the intermediary holder, 108 has a special groove, 112 designed to hold the wider base, 114 of the floss holder, 8 seen in FIG. 48, in order to assemble and secure the floss holder, 8. The floss holder, 8 has to be inserted laterally, as in FIG. 50, with the base edge 114 which extends off the sides of the base of the floss holder, and then rotated so that the arms, 12 embrace the intermediary holder, and interlock into the matching grooves, 110 on the sides of the intermediary holder.

In FIG. 52 there is shown another embodiment of the intermediary holder, 108 and which is endowed with a special shape that enables it to flex the arms, 12 of the floss holder from FIG. 53, sideways bringing the arms tips closer to each other, when floss holder is pushed against the lateral sides of the teeth, as in FIGS. 59 and 60, when the dental floss, 10 is able to adhere optimally to the natural shape of the teeth.

In FIGS. 55 and 56, the sectional views XIX-XIX and XX-XX through the intermediary holder from FIG. 54 show its concave, 120 and respectively convex, 122 contact shapes.

In FIG. 54 is displayed the assembly method where the floss holder, 8 is introduced from the side and then rotated towards the upper side of the intermediary holder, 108 when floss holder gets anchored but still keeps a degree of freedom to swing when the horns, 116 are constrained to an area, 120 seen in FIG. 55 by the special concave shape of the intermediary holder. When pushed against the lateral walls of the teeth, the floss holder, 8, will have the horns pushed away from each other and that will force the tips of the jaws to flex closer to each other, as in FIGS. 59 and 60.

FIG. 61 discloses another embodiment of a swiveling intermediary holder endowed with anisotropic lateral flexibility due to a thinner area, 36 in the base of the arms, and with additional elasticity due to the elastomer coating, 38 over the said thinner areas. The arms, 115 have a specially designed groove, 117 to engage through a clipping mechanism, 111, with a thinner floss holder, 8, that has lateral hooks, 109 in continuation of its arms, 12 for clipping purpose, and rounded gripping edges, 44, both meant to secure the said floss holder onto the intermediary holder. When floss holder is assembled, the slightly opened arms, 115 of the intermediary holder stretch the dental floss, 10, and its arched base, 119, increases tension like a spring, being pressed against the base of the intermediary holder. To extract the floss holder, the user has to press on the clipping wings, 111 to release the hooks, 109, which allows tension in the arched spring to eject the floss holder.

In FIG. 66, there is shown a side view of an ergonomic flossing device with a sliding mechanism for remote controlled step by step rotational advancement of the floss holder.

As seen in the back view in FIG. 67, each time the user pulls the step advancement slider, 142 from the grip, 146 the specially designed hook, 158 present at the tip of the slider, as seen in FIG. 68, pulls the toothed-wheel, 162 by one step in one direction.

The spring-like elastomer, 148 between the end of the slider, 150, and the joint area, 152 on the back of the handle, 4, automatically pushes the hook 158 to its locked state without generating any rotation movement in the toothed-wheel due to the one way clipping lock, 164, therefore securing the floss holder 8, in the desired working position, due to the complementary toothed shape, 160 at the end of the step slider, 142.

The step slider, 142 has a bottom clipping extension, 154 that fits into the sliding path, 156, as seen in the back view of the flossing device from FIG. 67.

FIGS. 69 and 70 display an enlarged back view of the step advancement mechanism where the toothed-wheel, 162 is in one piece with the floss holder.

In FIG. 71 there is shown an enlarged back view of an alternative embodiment of our flossing device similar to the one described in FIG. 69, but where the toothed-wheel, 162 is a separate element of the product, and has a perforation in its cut out section which matches the profile, 166 in the neck, 17 of the floss holder which is secured so that it will drive synchronically, at each sequential step advancement.

FIG. 72 presents a front view of the floss holder, with a lateral flexibility mechanism similar to the one from FIG. 23, with XXVI-XXVI cross-sectional views through the head portion, 6, the hook, 158 of the step slider 142, and the one way clipping lock, 164. The separate toothed-wheel, 162 has a specially designed circular protrusion edge, 168 at its lower side to enable clipping it secured into the perforation 70 in the head portion, 6.

FIG. 73 presents a flossing device unit where the head portion is mounted on a grasping means, 4 that conveys an electromechanical movement to the swiveling floss holder endowed with said lateral flexibility. When the switch, 173 is in the on position, the electric engine, 175 is powered by the battery, 171, and generates a vibration in the handle due to the asymmetric weight, 174 attached to the rotor of the said engine.

FIGS. 74 and 75 show disposable flossing device with substantially short grasping means, 4 where the swiveling floss holder, 8, endowed with lateral flexibility, has a protrusion, 17 or respectively a opening 102 for clipping into a complementary shape on the head portion, as attaching means.

FIGS. 76 to 86 disclose several optional heads with different additional tools that can be attached to a handle, 2 similar to the ones described for the flossing device, through the means of a base, 170 that is mounted onto the head portion, 6 such that it can swivel, therefore offering more options to the end user. The tools can be attached in swinging manner through a bolt protrusion, 174 into a matching groove, 172, or simply be in one piece with the base, 170. This way, it can be suggested to incorporate a variety of replaceable heads in the above-described flosser of the present invention, such as for an oral mirror, 176 shown in FIG. 76, a tongue cleaner, 178 shown in FIG. 79, a gum massager, 180 shown in FIG. 81, a plaque remover, 182 shown in FIG. 83, an interdental brush, 184 shown in FIG. 85, or a toothbrush, 186 shown in FIG. 86.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A dental flossing device comprising:
   a handle having:
      a head portion; and
      a grasping portion;
   a floss holder comprising:
      a base portion;
      a pair of spaced-apart arms projecting from said base portion; and
      at least one length of dental floss between said spaced-apart arms;
   wherein said floss holder is rotatably-attached to said head portion, and
   wherein each spaced-apart arm comprises at least one convoluted portion along its length, and near the base portion, such that said spaced-apart arms have enhanced flexibility perpendicular to the plane of the floss holder when lateral pressure is applied to the dental floss in a direction laterally perpendicular to the dental floss against a tooth.

2. A dental flossing device according to claim 1,
   wherein said floss holder has an upper face having a central area with a shoulder reinforcement for a fit anchoring to said head portion.

3. A dental flossing device according to claim 1, wherein said base portion comprises a post projecting from said base portion, wherein said head portion comprises a sleeve, and wherein said base portion is attached to said head portion by means of said sleeve engaging said post.

4. A dental flossing device according to claim 1, wherein said floss holder is attached demountably to said head portion of said handle.

5. A dental flossing device according to claim 1, wherein said arms of said floss holder are "C" shaped.

6. A dental flossing device according to claim 1, wherein said at least one length of dental floss is two lengths of dental floss.

7. A dental flossing device according to claim 1, wherein said head portion is attached to said grasping portion such that it is rotatable around its own axis through a preset number of positions.

8. A dental flossing device according to claim 1, wherein said grasping portion comprises an electromechanical vibrator.

9. A dental flossing device according to claim 1, wherein said floss holder further comprises a neck having a groove, said groove being aligned in a direction generally perpendicular to the direction of said floss so that when the neck is inserted into a hole in said head portion, said groove is compressed, such that said arms of said floss holder are extended, thereby increasing dental floss tension.

10. A dental flossing device according to claim 1, wherein movement of said spaced-apart arms closer to each other, and out of the plane of said floss holder is adapted to enable said dental floss to slacken such that it can adhere to the contour of said tooth.

11. A dental flossing device comprising:
   a handle having
      a head portion comprising a sleeve; and
      a grasping portion;
   a floss holder comprising
      a base portion comprising a post protruding from said base portion;
      a pair of spaced-apart arms projecting from said base portion; and
      at least one length of dental floss between said spaced-apart arms, wherein said floss holder is rotatably-attached to said head portion, wherein said post protruding from said base portion is engaged in said sleeve in said head portion, wherein each spaced-apart arm comprises at least one convoluted portion along its length, and near the base portion, and wherein said post and base portion have a groove along at least part of their axial length, said groove being aligned in a direction generally perpendicular to the direction of said floss, and having non parallel internal faces such that said groove width is larger at its outer ends than at its center, the internal faces of said groove being adapted to enable said spaced-apart arms to move closer to each other perpendicular to the plane of the floss holder when lateral pressure is applied to the dental floss in a direction laterally perpendicular to the dental floss against a tooth.

12. A dental flossing device according to claim 11, wherein said floss handle has one or more ridges protruding into said sleeve in said head portion, designed to engage in grooves present on said post portion of said floss head, in order to retain said floss holder in a position for securing by said grasping portion.

13. A dental flossing device according to claim 11, wherein contact of said internal faces of said groove limits movement of said spaced-apart arms closer to each other.

14. A dental flossing device according to claim 11, wherein said floss holder post is detachable from said head portion only when said groove in said post is oriented in a preset direction.

15. A dental flossing device according to claim 11, further comprising locking means for securing said post into said head portion wherein the locking means requires said groove to be oriented in a preset direction.

16. A dental flossing device according to claim 11, wherein said arms of said floss holder are "C" shaped.

17. A dental flossing device according to claim 11, wherein said at least one length of dental floss is two lengths of dental floss.

18. A dental flossing device according to claim 11, wherein movement of said spaced-apart arms closer to each other, and out the plane of said floss holder is adapted to enable said dental floss to slacken such that it can adhere to the contour of said tooth.

* * * * *